(12) United States Patent
Zheng et al.

(10) Patent No.: US 11,667,670 B2
(45) Date of Patent: Jun. 6, 2023

(54) CORN PROTEIN RETENTION DURING EXTRACTION

(71) Applicant: CARGILL, INCORPORATED, Wayzata, MN (US)

(72) Inventors: Guo-Hua Zheng, Centerville, OH (US); Hadi Yehia, Beavercreek, OH (US)

(73) Assignee: CARGILL, INCORPORATED, Wayzata, MN (US)

( * ) Notice: Subject to any disclaimer, the term of this patent is extended or adjusted under 35 U.S.C. 154(b) by 350 days.

(21) Appl. No.: 16/649,121

(22) PCT Filed: Sep. 11, 2018

(86) PCT No.: PCT/US2018/050447
§ 371 (c)(1),
(2) Date: Mar. 19, 2020

(87) PCT Pub. No.: WO2019/060179
PCT Pub. Date: Mar. 28, 2019

(65) Prior Publication Data
US 2020/0291062 A1    Sep. 17, 2020

Related U.S. Application Data

(60) Provisional application No. 62/561,287, filed on Sep. 21, 2017.

(51) Int. Cl.
| | | |
|---|---|---|
| C07K 14/415 | (2006.01) | |
| C07K 1/14 | (2006.01) | |
| A23J 1/12 | (2006.01) | |
| C07K 1/30 | (2006.01) | |
| C07K 14/425 | (2006.01) | |

(52) U.S. Cl.
CPC ............... *C07K 1/145* (2013.01); *A23J 1/12* (2013.01); *C07K 1/30* (2013.01); *C07K 14/415* (2013.01); *C07K 14/425* (2013.01); *B01D 2251/00* (2013.01)

(58) Field of Classification Search
CPC .......... C07K 14/25; C07K 1/30; C07K 1/145; B01D 2251/00; A23J 1/12
See application file for complete search history.

(56) References Cited

U.S. PATENT DOCUMENTS

| | | |
|---|---|---|
| 2,105,760 A | 1/1938 | Swallen |
| 2,120,946 A | 6/1938 | Swallen |
| 2,124,284 A | 7/1938 | Bole |
| 2,133,591 A | 10/1938 | Swallen |
| 2,156,928 A | 5/1939 | Swallen |
| 2,218,221 A | 10/1940 | Schopmeyer |
| 2,227,605 A | 1/1941 | Swallen |
| 2,360,381 A | 10/1944 | Walsh |
| 2,384,388 A | 9/1945 | Monte |
| 2,414,195 A | 1/1947 | Evans |
| 2,704,257 A | 3/1955 | Sollano |
| 4,018,936 A | 4/1977 | Garbutt |
| 4,024,120 A | 5/1977 | Phillips |
| 4,108,847 A | 8/1978 | Creinin |
| 4,213,941 A | 7/1980 | Boomer |
| 4,265,925 A | 5/1981 | Campbell |
| 4,361,651 A | 11/1982 | Keim |
| 4,624,805 A | 11/1986 | Lawhon |
| 4,716,218 A | 12/1987 | Chen |
| 5,254,673 A | 10/1993 | Cook |
| 5,254,763 A | 10/1993 | Gill |
| 5,367,055 A | 11/1994 | Takahashi |
| 5,410,021 A | 4/1995 | Kampen |
| 5,498,431 A | 3/1996 | Lindner |
| 5,510,463 A | 4/1996 | Takahashi |
| 5,580,959 A | 12/1996 | Cook |
| 5,602,286 A | 2/1997 | Muralidhara |
| 5,798,446 A | 8/1998 | Neumuller |
| 5,847,238 A | 12/1998 | Muralidhara |
| 6,169,217 B1 | 1/2001 | Cheryan |
| 6,433,146 B1 | 8/2002 | Cheryan |
| 6,602,985 B1 | 8/2003 | McInnis |
| 6,610,831 B1 | 8/2003 | McInnis |
| 6,846,909 B2 | 1/2005 | Mairal |
| 7,045,607 B2 | 5/2006 | Cheryan |
| 7,829,680 B1 | 11/2010 | Sander |
| 8,795,760 B2 | 8/2014 | Lawton, Jr. |
| 9,226,515 B2 | 1/2016 | Slabbekoorn |
| 2001/0009040 A1 | 7/2001 | Duvick |
| 2002/0183490 A1 | 12/2002 | Cheryan |

(Continued)

FOREIGN PATENT DOCUMENTS

| | | |
|---|---|---|
| CN | 1899076 A | 1/2007 |
| CN | 101703146 A | 5/2010 |

(Continued)

OTHER PUBLICATIONS

Anderson, Timothy James, "Extraction of zein from corn co-products", Master thesis, 2011, Food Science and Technology, Iowa State University, pp.i-v and 1-114.
"The Corn Refining Process" 2 pages, downloaded from https://corn.org/wp-contentiuploads/2009/11/CornRefiningProcess.pdf (Year: 2009).
(International Standard ISO) Native starch—Determination of starch content—Ewers polarimetric method. ISO 10520. Sep. 1997.
(Solvay Interox) "Hydrogen Peroxide Controlling reduced sulphur compounds" Mar. 2011; [retrieved May 25, 2017]. Retrieved from the Internet: <URL:http://www.solvay.com/au/en/binaries/Controlling%20reduced%20suphur%20species-202502.pdf>.
Anderson, "Detoxification of Aflatoxin-Contaminated Corn", Proc. Symp. held in Atlanta, Ga., Jan. 26-27, 1982. Soth. Coop. Ser. Bull. 279:87-90 (Year: 1982).

(Continued)

*Primary Examiner* — Jeanette M Lieb

(57) ABSTRACT

Described herein is a method of maintaining corn protein yield during extraction, comprising obtaining a corn gluten material, washing the corn gluten material to remove non-protein components with an ethanol-water solvent comprising at least 85 wt % ethanol to obtain a corn protein concentrate product, wherein the loss of corn protein content during extraction is less than 25% of total corn protein.

10 Claims, 17 Drawing Sheets

(56) References Cited

U.S. PATENT DOCUMENTS

| | | |
|---|---|---|
| 2003/0066106 A1 | 4/2003 | Strissel |
| 2003/0198725 A1 | 10/2003 | Cardenas |
| 2004/0009263 A1 | 1/2004 | Liu |
| 2005/0008759 A1 | 1/2005 | Nie |
| 2005/0064079 A1 | 3/2005 | Allen |
| 2005/0074538 A1 | 4/2005 | Elder |
| 2006/0057275 A1 | 3/2006 | Wu |
| 2006/0182857 A1 | 8/2006 | Thorre |
| 2006/0240169 A1 | 10/2006 | Heydtmann |
| 2007/0087101 A1 | 4/2007 | Gusek |
| 2007/0172914 A1 | 7/2007 | Slabbekoorn |
| 2008/0102502 A1 | 5/2008 | Foody |
| 2008/0118626 A1 | 5/2008 | McWilliams |
| 2009/0041901 A1 | 2/2009 | Elmusa |
| 2009/0053368 A1 | 2/2009 | Fox |
| 2009/0148589 A1 | 6/2009 | Fox |
| 2009/0209423 A1 | 8/2009 | Slabbekoorn |
| 2009/0215990 A1 | 8/2009 | Cheryan |
| 2010/0016554 A1 | 1/2010 | Cheryan |
| 2010/0159521 A1 | 6/2010 | Cirakovic |
| 2010/0221387 A1 | 9/2010 | Marcelo |
| 2010/0233756 A1 | 9/2010 | Sunvold |
| 2012/0027890 A1 | 2/2012 | Cerne |
| 2013/0273219 A1 | 10/2013 | Baier |
| 2014/0123855 A1 | 5/2014 | Lawton, Jr. |
| 2014/0161962 A1 | 6/2014 | Boebel |
| 2014/0193547 A1 | 7/2014 | Brown |
| 2014/0220217 A1 | 8/2014 | Brown |
| 2014/0271928 A1 | 9/2014 | Rehage |
| 2014/0303348 A1 | 10/2014 | Lawton, Jr. |
| 2014/0343259 A1 | 11/2014 | Bleyer |
| 2014/0356510 A1 | 12/2014 | Schweizer |
| 2015/0201647 A1 | 7/2015 | Fosdick |
| 2016/0165932 A1 | 6/2016 | Armentrout |
| 2016/0286840 A1 | 10/2016 | Shane |
| 2017/0354737 A1 | 12/2017 | Harel |
| 2019/0029295 A1 | 1/2019 | Mielgo Iza |
| 2020/0236977 A1 | 7/2020 | Li |

FOREIGN PATENT DOCUMENTS

| | | |
|---|---|---|
| CN | 101560252 B | 1/2012 |
| CN | 102669406 A | 9/2012 |
| CN | 103059116 A | 4/2013 |
| CN | 103554278 A | 2/2014 |
| CN | 104938763 A | 9/2015 |
| CN | 105541982 A | 5/2016 |
| CN | 106009766 B | 11/2017 |
| EP | 0510537 B1 | 7/1997 |
| EP | 0648078 B1 | 4/2001 |
| EP | 2491794 A1 | 8/2012 |
| EP | 2401920 B1 | 2/2013 |
| EP | 3075259 A1 | 10/2016 |
| EP | 3375290 A2 | 9/2018 |
| FR | 2902607 B1 | 6/2019 |
| JP | 5754564 A | 4/1982 |
| JP | 63185998 A | 8/1988 |
| JP | 63185999 A | 8/1988 |
| JP | 2011097928 A | 5/2011 |
| JP | 4750901 B2 | 8/2011 |
| JP | 06189687 B2 | 3/2015 |
| KR | 101409213 B1 | 6/2014 |
| WO | 8809622 A1 | 12/1988 |
| WO | 1991012730 A2 | 9/1991 |
| WO | 9312667 W | 7/1993 |
| WO | 1998044807 A1 | 10/1998 |
| WO | 0150882 W | 7/2001 |
| WO | 2005074704 A1 | 8/2005 |
| WO | 2005091995 A2 | 10/2005 |
| WO | 2007019227 A1 | 2/2007 |
| WO | 2009155350 A1 | 12/2009 |
| WO | 2014186567 A1 | 11/2014 |
| WO | 2015004448 A1 | 1/2015 |
| WO | 2015109276 A1 | 7/2015 |
| WO | 2016154441 A1 | 9/2016 |
| WO | 2017011625 A1 | 1/2017 |
| WO | 2017040273 A2 | 3/2017 |
| WO | 2017058501 A1 | 4/2017 |
| WO | 2017081347 A2 | 5/2017 |
| WO | 2017165748 A1 | 9/2017 |
| WO | 2017165756 A1 | 9/2017 |
| WO | 2017189322 A1 | 11/2017 |
| WO | 2018058150 A1 | 3/2018 |
| WO | 2018237030 A1 | 12/2018 |
| WO | 2019028263 A2 | 2/2019 |
| WO | 2019060179 A1 | 3/2019 |
| WO | 2019060673 A1 | 3/2019 |

OTHER PUBLICATIONS

Anderson, R. A.; "Detoxification of Aflatoxin-Contaminated Corn", Cereal Chemistry, 55, 87-90, Jan. 31, 1978.

Anderson, Timothy J., et al., "Development of New Method for Extraction of a-Zein from Corn Gluten Meal Using Different Solvents", Cereal Chem. 88(4): 356-362, 2011.

Anderson, Timothy J., et al., "Zein Extraction from Corn, Corn Products, and Coproducts and Modifications for Various Applications: A Review", Cereal Chem. 88(2): 159-173, 2011.

Argos et al. (in J. Biol Chem. vol. 217 (17): pp. 9984-9990, 1982).

Bookwalter Corn Distillers Grains and Other By-Products of Alcohol Production in Blended Foods. II. Sensory, Stability and Processing Studies, Cereal Chem. vol. 61, No. 6, 1984, 509-513.

Bryla, Marcin, et al., "Effects of pH and Temperature on the Stability of Fumonisins in Maize Products", Toxins 2017, 9, 88; doi:10.3390/toxins9030088.

Burns TD et al.: "Fumonisin concentrations and in vivo toxicity of nixtamalized Fusarium verticillioides culture material: Evidence for fumonisin-matrix interactions", Food and Chemical Toxicology, Pergamon, GB, vol. 46, No. 8, Aug. 1, 2008 (Aug. 1, 2008), pp. 2841-2848, XP022939030, ISSN: 0278-6915, DOI: 10.1016/J.FCT.2008.05.017.

CIELAB color space—Wikipedia; https://en.wikipedia.org/wiki/CIELAB_color_space; retrieved Oct. 5, 2019; 9 pages.

Database WPI, Week 198219, Thomson Scientific, London, GB; AN 1982-38049E, XP002794657, & JPS5754564A (Nippon Shokuhin Kako KK), Apr. 1, 1982 (Apr. 1, 1982).

Dickey, L.C., "Ethanolic Extraction of Zein from Maize", Industrial Crops and Products 13 (2001), Apr. 30, 2000, 67-76.

El-Hawwary et al. (in Agric. Res. Review 67 (4): 611-618, 1989).

Gomez, M.H., et al., "Changes in the Starch Fraction During Extrusion-cooking of Corn", Food Science, vol. 48, Issue 2 (Mar. 1983); pp. 378-381, XP055512137.

Gupta Ho et al.: "Plant Foods for Human Nutrition 52: Processing of maize germ oil cake into edible food grade meal and evaluation of its protein quality", Plant Foods for Human Nutrition, vol. 52, Mar. 1, 1998 (Mar. 1, 1998), pp. 1-8, XP055808466, Retrieved from the Internet: URL:https://link.springer.com/content/pdf/10.1023/A:1008088822395.pdf>.

Hojilla-Evangelista M P et al, "Sequential Extraction Processing of High-Oil Corn", Cereal Chemistry, AACC International Inc, US, (Nov. 1, 2003), vol. 80, No. 6, ISSN 0009-0352, pp. 679-683, XP001185001.

Hojilla-Evangelista M et al: "Optimizing extraction of zein and glutelin-rich fraction during sequential extraction processing of corn", Cereal Chemistry, AACC International Inc, US, vol. 80, No. 4, Jan. 1, 1979 (Jan. 1, 1979), pp. 481-484, XP009092386, ISSN: 0009-0352, DOI:10.1094/CCHEM.2003.80.4.481.

Hojilla-Evangelista MP et al.: "Characterization of Protein Extracted From Flaked, Defatted, Whole Corn By the Sequential Extraction Process!", Journal of the American Oil Chemists Society, Springer, DE, vol. 69, No. 3, Mar. 1, 1992 (Mar. 1, 1992), pp. 199-204, XP000245384, ISSN: 0003-021X, DOI: 10.1007/BF02635886.

Ho-Soo Lim et al, "Comparison of four different methods for the determination of sulfites in foods marketed in South Korea", Food Additives & Contaminants: Part A, (Jan. 16, 2014), vol. 31, No. 2, doi:10.1080/19440049.2013.857048, ISSN 1944-0049, pp. 187-196, XP055627607.

(56) References Cited

OTHER PUBLICATIONS

Inglett, GE et al. High-shear, Jet-cooking, and Alkali Treatment of Corn Distillers' Dried Grains to Obtain Products with Enhanced Protein, Oil and Phenolic Antioxidants. Food Science and Technology International, vol. 16, No. 4, Jul. 9, 2010, pp. 297-308.

Ivanova et al. "Producing of Feed protein concentrates as a method for rational utilization of recyclable fish materials" Food processing Industry Issue 12 2011 abstract.

Johansson, D et al., Influence of Surface lipids in Commercial Zein on Microstructure and Rheological Properties of Gluten-Free Dough, Annual Transactions of the Nordic Theology Society, vol. 20, 2012, pp. 247-251.

Johnson et al., "Optimizing Extraction of Zein and Glutelin-Rich Fraction During Sequential Extraction Processing of Corn", Cereal Chem. vol. 80, No. 4, 2003, 481-484.

Lawton, JW, "Zein: A History of Processing and Use", Cereal Chemistry., (2002), vol. 79, No. 1, pp. 1-18, XP009092326.

Mao et al. (in Int. J. MoL Sci. 15, 2003-2014, 2014).

Mary A. Dombrink-Kurtzman et al.: "Effect of Nixtamalization (Alkaline Cooking) on Fumonisin-Contaminated Corn for Production of Masa and Tortillas", Journal of Agricultural and Food Chemistry, vol. 48, No. 11, Nov. 1, 2000 (Nov. 1, 2000), pp. 5781-5786, XP055564817, us ISSN: 0021-8561, DOI: 10.1021/jf000529f.

McNeillie, Alastair, and Juli Bieser. "Hydrogen peroxide uses for the year 2000." Food Processing Oct. 1993: 59+. Business Insights: Global Web. Feb. 9, 2016.

Momany, Frank A., et al., "Structural Characterizations of a Zein", Journal of Agricultural and Food Chemistry, 2006, 54, 543-547.

Nielsen et al. (in Cereal Chemistry, vol. 47 (5): pp. 501-512, 1970).

Parris Net Al: "Extraction and Solubility Characteristics of Zein Proteins From Dry-Milled Corn", Journal of Agricultural and Food Chemistry, American Chemical Society, US, vol. 49, No. 8, Aug. 1, 2001 (Aug. 1, 2001), pp. 3757-3760, XP001071383, ISSN: 0021-8561, DOI: 10.1021/JF0011790.

Paulson et al. (1984) Can. Inst. Food Sci. Technol. J. 17:202-208.

R. Dixon Phillips et al., "Corn Protein Concentrate: Functional and Nutritional Properties", Journal of Food Science, US, (1979), vol. 44, No. 4, doi:10.1111/j.1365-2621.1979.tb03470.x, ISSN 0022-1147, pp. 1152-1155, XP055495372.

Reiners et al., "Corn Proteins: Potential for their Industrial Use" 58th Annual American Association of Cereal Chemists, 1973.

Ren Ting-ting, et al., "Research on extraction of zein and its functional properties and application", Science and Technology of Cereals, Oils and Foods. vol. 22. Issue 3, May 21, 2014.

Selling et al.: "The effect of extrusion processing on Zein", Polymer Degradation and Stability, Bark I Ng, GB, vol. 95, No. 12, Dec. 1, 2010 (Dec. 1, 2010), pp. 2241-2249, XP027527379, ISSN: 0141-3910.

Sessa, David J., et al., "Improved Methods for Decolorizing Corn Zein", Industrial Crops and Products 18 (2003), 55-65.

Shukla et al: "Zein: the industrial protein from corn", Industrial Crops and Products, Elsevier, NL, vol. 13, No. 3, Jan. 1, 2001 (Jan. 1, 2001), pp. 171-192, XP002459554, ISSN: 0926-6690, DOI: 10.1016/S0926-6690 (00)00064-9.

Sydenham et al. J. Agric. Food Chem. 1995, vol. 43, pp. 1198-1201 (Year: 1995).

Takahara et al., JP4750901(B2)—English Translation, pp. 1-55 (Year: 2011).

Wu, Y et al., Balancing of sulfur storage in maize seed. BMC Plant Biology, vol. 12, May 30, 2012, 77.

Wu, YV et al., Protein-Rich Residue from Corn Alcohol Distillation; Fractionation and Characterization, Cereal chemistry. vol 58, No. 4, Apr. 1981, pp. 343-347.

CORN PROTEIN RETENTION DURING EXTRACTION

CROSS-REFERENCE TO RELATED APPLICATIONS

This application is a national phase application of International Application No. PCT/US2018/050447, filed Sep. 11, 2018, which claims the benefit of U.S. Provisional Patent Application No. 62/561,287, filed Sep. 21, 2017, each of which is hereby incorporated by reference in its entirety.

TECHNICAL FIELD

This disclosure relates to concentrated corn protein and methods of making concentrated corn protein.

BACKGROUND

For over 100 years, corn wet milling has been used to separate corn kernels into products such as starch, protein, fiber and oil. Corn wet milling is a two-stage process that includes a steeping process to soften the corn kernel to facilitate the next wet milling process step that result in purified starch and different co-products such as oil, fiber, and protein. Further corn processing methods are now being investigated to further purify the protein co-product for incorporation into food-grade products, specifically. A combination of increasing interest on the part of consumers for protein in their diet and increasing concerns about the cost and availability of animal derived proteins is causing food companies to look increasingly for new sources of protein.

SUMMARY

Described herein is a method of maintaining corn protein yield during extraction, comprising obtaining a corn gluten material, washing the corn gluten material to remove non-protein components with an ethanol-water solvent comprising at least 85 wt % ethanol to obtain a corn protein concentrate product, wherein the loss of corn protein content during extraction is less than 25% of total corn protein.

FIGURES

FIGS. 1A, 1B, 1C, and 1D show protein solubilization is promoted by lower ethanol concentrations and higher temperatures (25° C. left panel (1A, 1C); 42.5° C. right panel (1B, 1D)) during extraction.

DETAILED DESCRIPTION

Figure 1A:
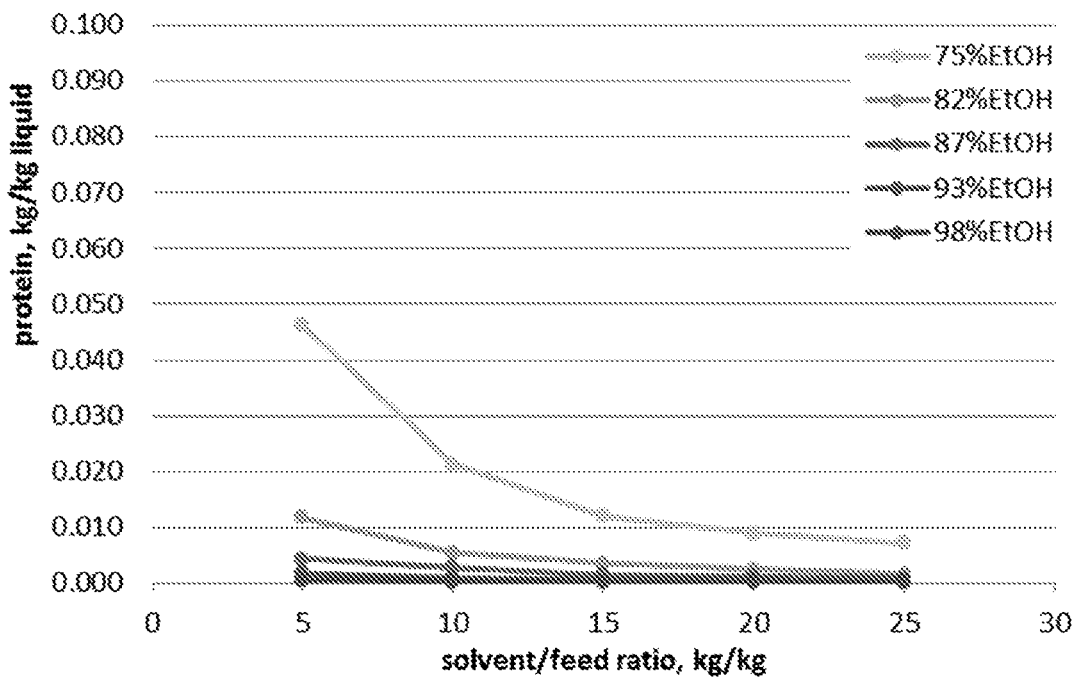

Protein ingredients are among the more expensive to prepare in high concentration. Often starting from a low-concentration natural product, many food proteins are prepared from by-products of processes intended to recover other components. For example, soy protein isolate is prepared from soy solids remaining after extraction of the oil fraction. Whey protein is prepared from soluble protein remaining after formation and pressing of cheese.

The corn protein described herein is prepared from a corn material, preferably a corn gluten material, which is a by-product of starch production in a wet milling process. The corn gluten material described herein is not destarched, hence contains a significant amount of starch granules (approximately 20% dry weight basis). Furthermore, the corn gluten material described herein comprises between 50 wt % to 70 wt % corn protein on a dry weight basis, and in preferred aspects comprises 60 wt % to 70 wt % corn protein on a dry weight basis. The corn gluten material described herein can be in a wet-cake form typically comprising 50-70 wt % moisture, or alternatively in a dried form comprising 3-6 wt % moisture.

The corn gluten material described herein optionally can be heat treated and/or treated with sulfite-neutralizing agents such as hydrogen peroxide, which not only can have a positive impact on corn protein yield but can also reduce sulfite levels commonly found in corn gluten materials. Such heat treatment can occur at temperatures ranging from 55° C. to about 85° C., preferably 60-80° C., and most preferably 65-75° C. Various sulfite-neutralizing agents such as oxidizing agents can be used to improve corn protein yield and to reduce free sulfite in the final corn protein products. Among sulfite-neutralizing agents, oxidizing agents specifically hydrogen peroxide is preferred. Hydrogen peroxide can be added to the corn gluten material in amounts that sufficiently neutralize free sulfite contained in the corn gluten material. Hydrogen peroxide is added at molar ratios of up to 5.0, preferably at molar ratio of up to 2.0 and more preferably at molar ratio of 1.0-1.5 to that of free sulfite contained in the corn gluten material. It is preferred that hydrogen peroxide is added to the corn gluten material with at least 15 min thorough mixing prior to washing. Heating treatment can be applied after the addition of hydrogen peroxide to optimize their effects on protein yield and sulfite reduction.

Normally, corn gluten material contains lipids (free fatty acids, phospholipids, sterols, tri-, di- and monoglycerides, etc.), pigments (lutein, beta-carotene, zeaxanthin, etc.), soluble carbohydrates (glucose, maltose, maltotriose and higher oligomers of glucose), organic acids (acetic, propionic, succinic, etc.) and in some circumstances mycotoxins (aflatoxin, zearalenone, etc.). Thus the corn protein material is at risk of generating soapy or rancid flavors from the lipids, astringent or sour flavors from the organic acids, undesirable colors in foods that contain the corn gluten material or health risks from the mycotoxins. Converting the corn gluten material from a form suitable for feed to a form desirable for food requires maximum removal of the lipid, pigment, mycotoxin and organic acids and a maximum retention of corn protein.

Because protein ingredients can be expensive, it is beneficial to prepare these corn protein ingredients at as low a cost as possible. Developing a process to achieve a desired final corn protein product composition with the highest protein yield and lowest cost is critical. In this context, the protein must be useful in foods for human and animal consumption, so the optimization is not simply a function of achieving an acceptable chemical composition; the resulting ingredient must have a suitable functional behavior suitable for the food process and product it is used in. It is recognized that some foods intended for animals, like pet foods, have functionality requirements similar to those required for human foods.

Aspects herein describe the production of a corn protein product, specifically corn protein concentrate, comprising 55-85 wt % or 55-80 wt % corn protein on a dry weight basis.

The desired corn protein product comprises less than 2 wt % oil, preferably less than 1.5 wt % oil, and even more preferably less than 1.0 wt % oil, all on a dry basis.

The desired corn protein product is light in color with an "a*" color value ranging from 0 to 4, and more preferably 0 to 2, a "b*" color value ranging from 15 to 35, and more preferably 15 to 30, and an "L*" color value ranging from 70 to 90, and more preferably 80 to 90.

A general process for the production of such corn protein product has been described in pending patent applications PCT Patent Application No. PCT/US17/23999 (filed on Mar. 24, 2017), which is hereby incorporated by reference in its entirety. Described therein is a process by which corn gluten material undergoes a series of solvent washing steps to produce a corn protein product.

In the course of developing the process to prepare a corn protein product that meets expectations, it has been discovered that the water present in the process had a number of effects on the process and that good control of the water concentration at various stages of the process is desirable. For example, excess water in the extracting solvent, especially at elevated temperatures, dissolves a portion of the protein and removes it from the final corn protein product. This did not tend to diminish the purity of the final corn protein product, but it substantially decreased the protein yield. Under some conditions, greater than 35% of the protein is lost. While this protein could be recovered from the extract and returned to the main ingredient pool, this recovery requires additional equipment investment and expense in operations. It is more economical to prevent the dissolution of the protein in the initial extraction phase.

Another undesirable phenomena associated with protein processing is fouling of surfaces, especially heat-contact surfaces. It was discovered that the water concentration in the extraction process could have a significant effect on the tendency of the protein to stick to surfaces. Equipment could be modified, particularly designed to be oversized to manage this stickiness, but that increases both the capital and operating expenses of the operation. It is more economical to manage the water concentration to mitigate this effect.

A final undesirable outcome is obtained when the water concentration present in the extraction process creates a physical behavior of the finished ingredient that is undesirable. Too much or too little water during extraction can modify the susceptibility of the corn protein product to physical or chemical reaction during extraction or subsequent processing. Identifying and applying specific water concentrations can be used to create specific functionalities. Because foods and food processes have differing functional requirements, water management may also have the potential to impact certain functionalities.

Accordingly, the invention disclosed herein provides a method of maintaining corn protein yield during an extraction process to obtain a desirable corn protein concentrate product.

The extraction process includes the steps of obtaining a corn gluten material and washing the corn material with an ethanol-water solvent comprising at least 85 wt % ethanol to obtain a corn protein product. As previously described, it was found surprising that reducing water content during the extraction process provides enhanced corn protein yield. Accordingly, in more preferable aspects, the ethanol-water solvent comprises at least 90 wt % ethanol, and even more preferably at least 93 wt % ethanol, and most preferably at least about 97 wt % or 98 wt % ethanol. It is recognized that in a counter-current extraction system, the corn protein material will be exposed to a range of water concentrations. In such a case, the higher the concentration of ethanol making initial contact with the corn material, the more desirable an outcome.

The ethanol solvent to corn protein product ratio also impacts corn protein yield. Accordingly, the extraction process described herein preferably has a solvent to corn protein ratio ranging from 5:1 to 25:1 (kg/kg).

Temperature also surprisingly affects the corn protein yield, and it was found that lower extraction temperatures are more desirable. More specifically, the extraction method described herein occurs at temperatures ranging from about 5-50° C., even more preferably range from about 20-30° C., and yet more preferably 25-30° C.

As demonstrated in the examples below, heat and hydrogen peroxide treatments prior to washing step in combination with reducing water content and operating at lower temperatures during subsequent extraction step improves the corn protein yield such that the loss of protein during extraction is less than 25%, more preferably less than 15%, and even more preferably less than 5%, 4%, 3%, 2% or 1% of total corn protein. In other aspects, the loss of ranges between 10% and 25% of total corn protein, even more preferably between 10% and 20% of total corn protein, and even more preferably between 5% and 15% of total corn protein.

Total corn protein is determined as the total nitrogen analyzed by combustion multiplied by 6.25; the nitrogen is primarily in the form of amino acids. Corn protein yield is expressed as percent of the final corn protein product weight divided by the weight of the raw corn gluten material on a moisture-free basis (or dry weight basis, dwb). Corn protein yield index is calculated by multiplying percent final product yield with percent protein content in the final product on a dry weight basis. The corn protein yield index herein ranges from about 0.55 to about 0.75.

EXAMPLES

Example 1: Effect of Temperature and Ethanol Concentration on Protein Solubilization and Yield Corn gluten slurry was obtained from the Cargill corn milling plant in Dayton, Ohio. The corn gluten slurry was dewatered by filtering through Whatman #3 filter paper. The resulting wet cake, at about 60% moisture, was freeze-dried to a final moisture concentration of 4.97% determined by Mettler-Toledo moisture analyzer at 110° C. The freeze-dried material contained 64.0% protein (N×6.25) on an as-is basis. The freeze-dried material was ground in a Waring blender at low speed until ~3+ mm large pieces disappeared. The ground material (1.4000-6.0000 g) was weighed into 50-ml polypropylene test tubes with screw caps. Then aqueous ethanol solvent containing 2-25% deionized water (98-75% ethanol, weight-by-weight) was added to each test tube at solvent/solid (9% moisture) ratios of 5, 10, 15, 20 and 25 to create treatments with varying water concentrations in the extraction system and varying solvent/solid, water/solid, EtOH/solid, water/EtOH ratios as shown in Table 1.

TABLE 1

| | The solvent | | | | | |
|---|---|---|---|---|---|---|
| | | % (wt/wt) | Ratios, g/g | | | |
| % (wt/wt) EtOH used | g solvent/ g feed (as-is % DS) | EtOH in final solvent | solvent/ 100% DS | water/ 100% DS | EtOH/ 100% DS | EtOH/ water |
| 98 | 25 | 97.8 | 26.5 | 0.58 | 26.82 | 44.6 |
|    | 20 | 97.8 | 21.2 | 0.48 | 21.56 | 43.6 |
|    | 15 | 97.7 | 16.1 | 0.37 | 16.19 | 42.1 |
|    | 10 | 97.5 | 10.7 | 0.27 | 10.78 | 39.3 |
|    | 5  | 97.0 | 5.3  | 0.16 | 5.40  | 32.7 |
| 93 | 25 | 92.8 | 26.4 | 1.90 | 25.45 | 12.9 |
|    | 20 | 92.8 | 20.7 | 1.49 | 20.41 | 12.8 |
|    | 15 | 92.7 | 16.2 | 1.18 | 15.32 | 12.7 |
|    | 10 | 92.5 | 10.8 | 0.80 | 10.25 | 12.4 |
|    | 5  | 92.1 | 5.4  | 0.42 | 5.13  | 11.6 |
| 87 | 25 | 86.8 | 26.7 | 3.51 | 23.89 | 6.6  |
|    | 20 | 86.8 | 20.8 | 2.75 | 19.12 | 6.6  |
|    | 15 | 86.7 | 16.1 | 2.14 | 14.36 | 6.5  |
|    | 10 | 86.6 | 10.5 | 1.41 | 9.58  | 6.4  |
|    | 5  | 86.1 | 5.3  | 0.74 | 4.79  | 6.2  |
| 82 | 25 | 81.8 | 26.1 | 4.74 | 22.50 | 4.5  |
|    | 20 | 81.8 | 21.3 | 3.87 | 18.05 | 4.5  |
|    | 15 | 81.7 | 16.3 | 2.97 | 13.50 | 4.5  |
|    | 10 | 81.6 | 10.3 | 1.91 | 9.01  | 4.4  |
|    | 5  | 81.2 | 5.3  | 1.00 | 4.51  | 4.3  |
| 75 | 25 | 74.9 | 25.9 | 6.52 | 20.50 | 3.0  |
|    | 20 | 74.8 | 21.0 | 5.29 | 16.51 | 3.0  |
|    | 15 | 74.8 | 16.0 | 4.05 | 12.38 | 3.0  |
|    | 10 | 74.6 | 10.6 | 2.69 | 8.26  | 2.9  |
|    | 5  | 74.3 | 5.3  | 1.37 | 4.14  | 2.9  |

The screw-capped test tubes containing both testing material and solvent were horizontally placed in a shaker that was set at 100 rpm orbital motion and maintained at either 25° C. (ambient) or 42.5° C. for 60 min During the 60 min extraction, the solid was gently moving in the solvent inside the test tubes to allow thorough contacting of the solid particles with the solvent without excessive force to minimize physical break down of solid particles.

After 60 min extraction, the test tubes were centrifuged at 4,000 rpm for 5 min at ambient temperature. The liquid from each test tube was carefully transferred to pre-weighed test tubes to record its net weight. The liquid was analyzed for protein and other dry solids. For the analysis, about 2.00 ml of liquid was pipetted into pre-weighed ceramic Leco cells with tin inserts. The Leco cells were placed in a fume hood for about 4 hours to allow ethanol evaporation then placed into a vacuum oven set at 50° C. and 25-inches vacuum to dry. After weighing again for the calculation of dry solids, the Leco cells were analyzed for protein concentration (using nitrogen factor of 6.25) in a Leco nitrogen analyzer. Calculations of protein in the cake fraction obtained from initial centrifugation were made by subtracting those determined in the liquid fraction from those contained in the starting material. It was assumed that equilibriums were achieved after 60 min extraction treatment at both temperatures.

Figure 1B:
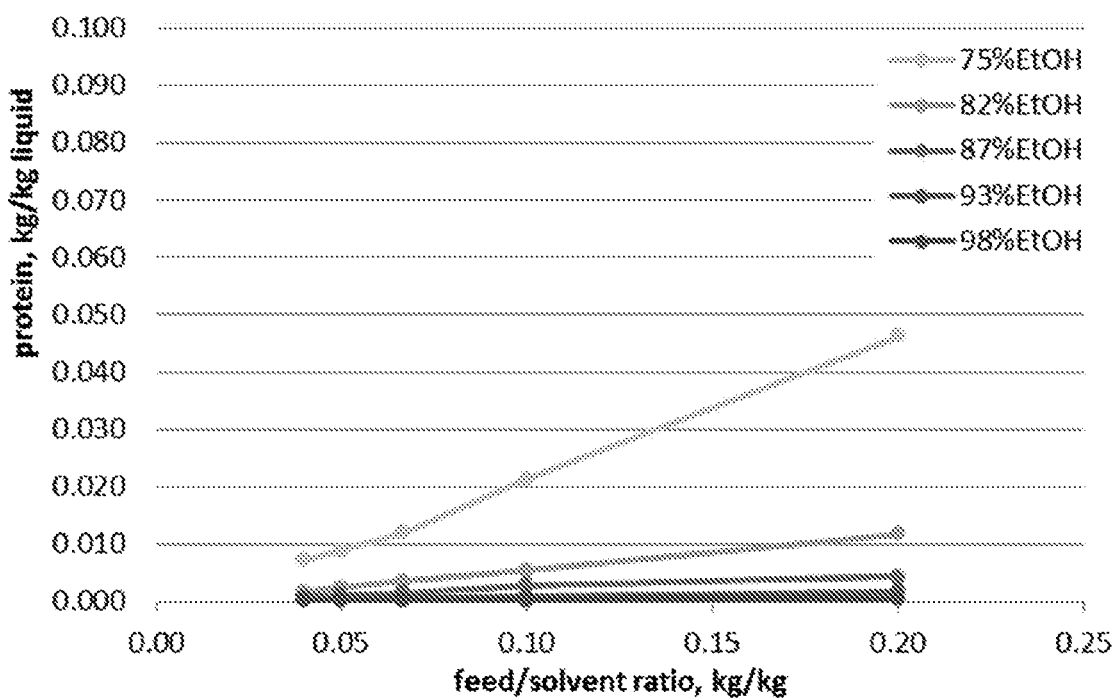
Figure 1C:
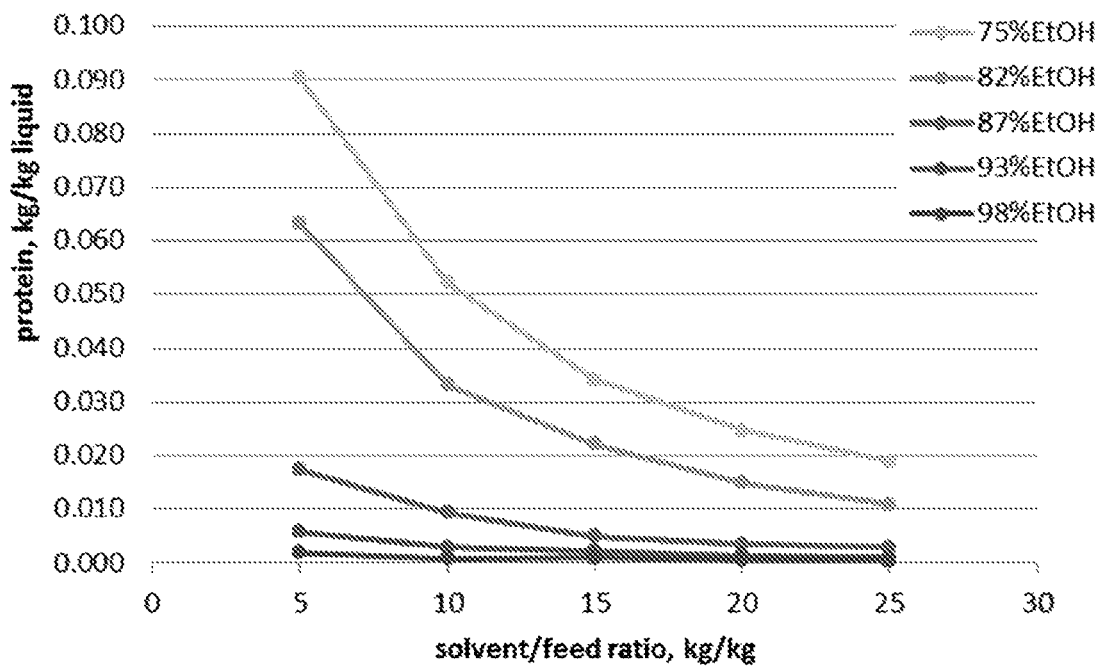
Figure 1D:
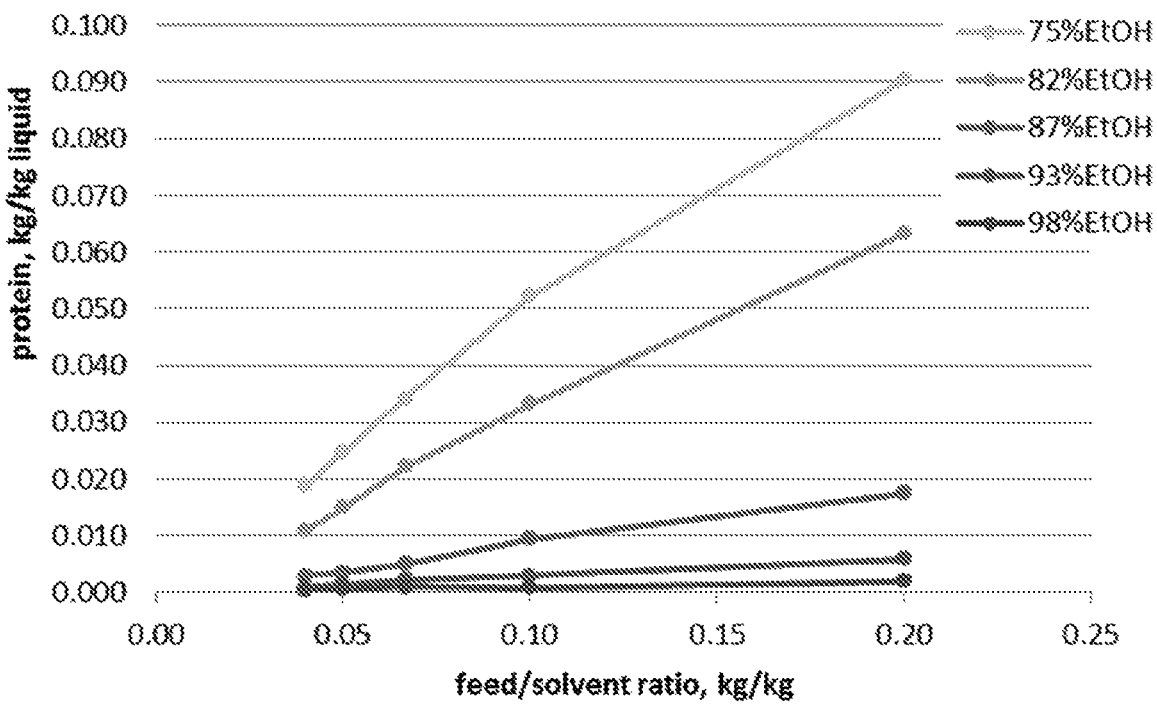

The results show protein solubilization (the desire is to avoid protein solubilization) is promoted by lower ethanol concentrations and higher temperatures (see FIGS. 1A and 1B). Protein extraction increases almost linearly as the feed-solvent ratio increases when viewed as solvent-feed there is a sharp decline in extraction as the ratio increases towards 10, with less sensitivity at higher ratios. Protein accounted for the majority of solubilized solids, particularly at higher temperatures with low ethanol concentrations.

Figure 2A:
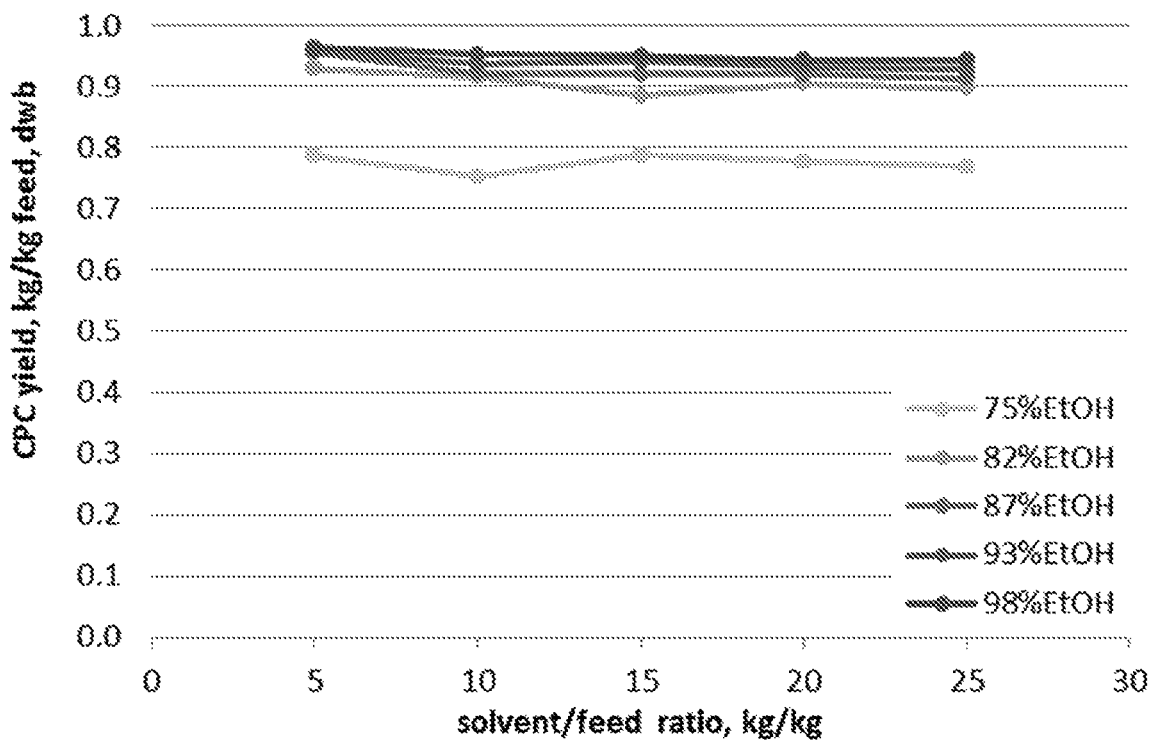
FIGS. 2A and 2B show the effects of ethanol concentration, solvent-feed ratio and temperature (25° C. left panel (2A); 42.5° C. right panel (2B)) during extraction on the yield of the final corn protein concentrate product.
Figure 2B:
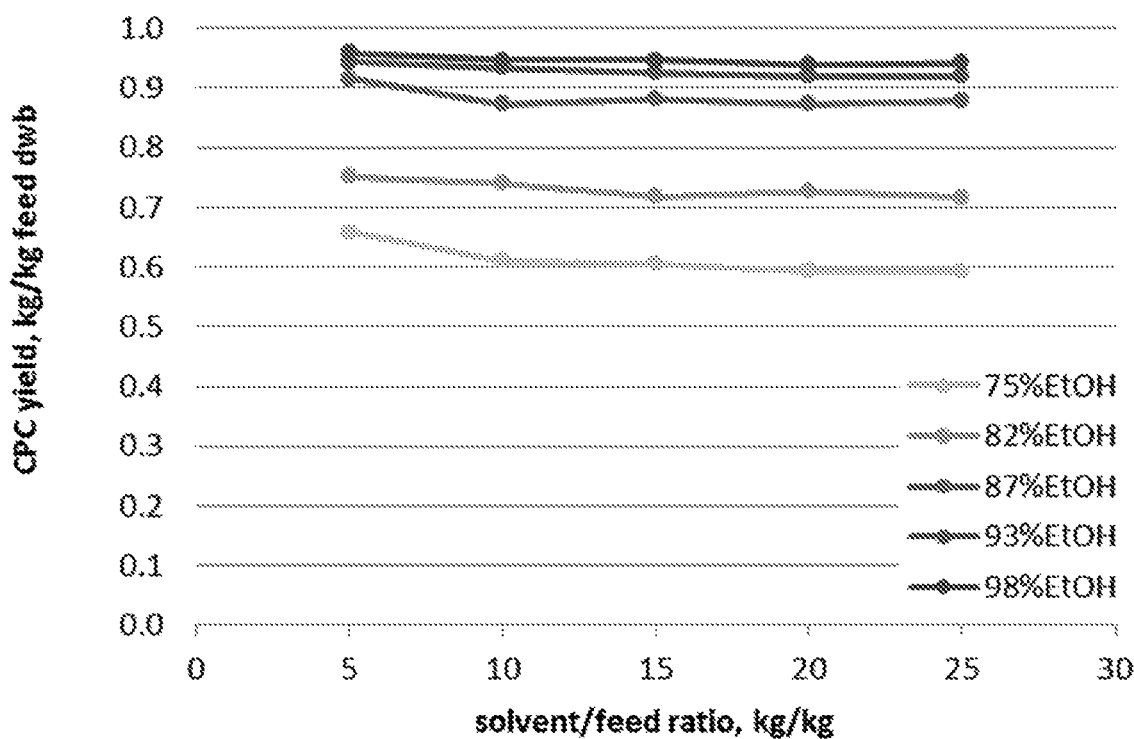
Figure 3A:
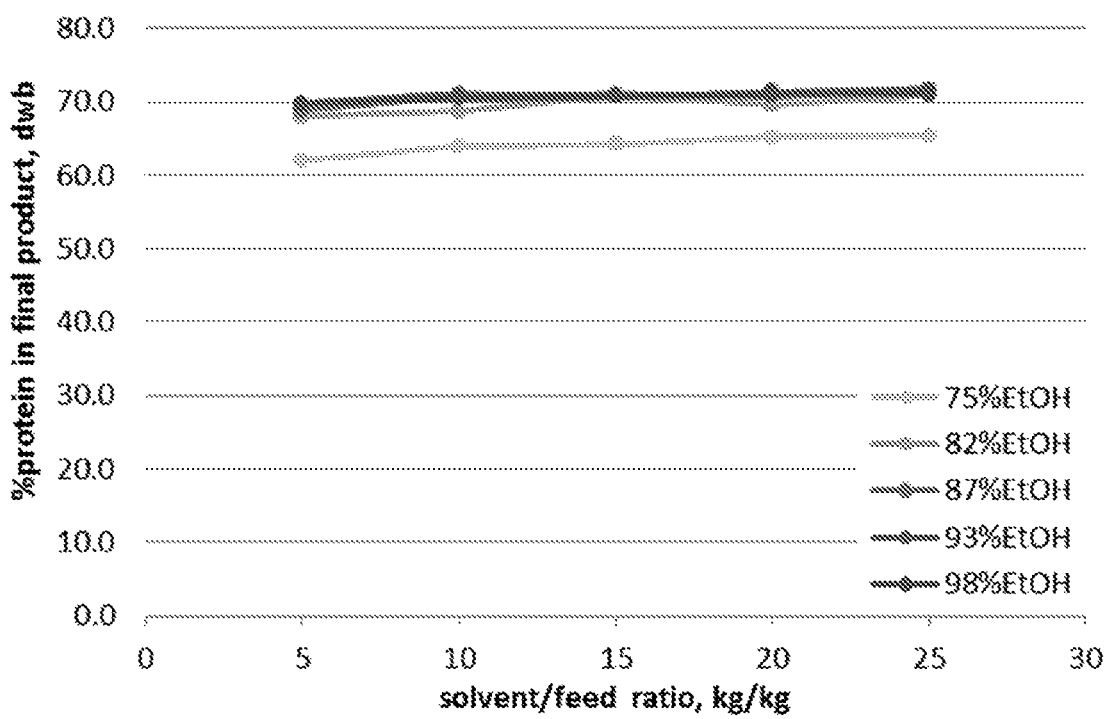
FIGS. 3A and 3B show ethanol concentration, solvent-feed ratio and temperature (25° C. left panel (3A); 42.5° C. right panel (3B)) during extraction impacts the composition of the final corn protein concentration product.
Figure 3B:
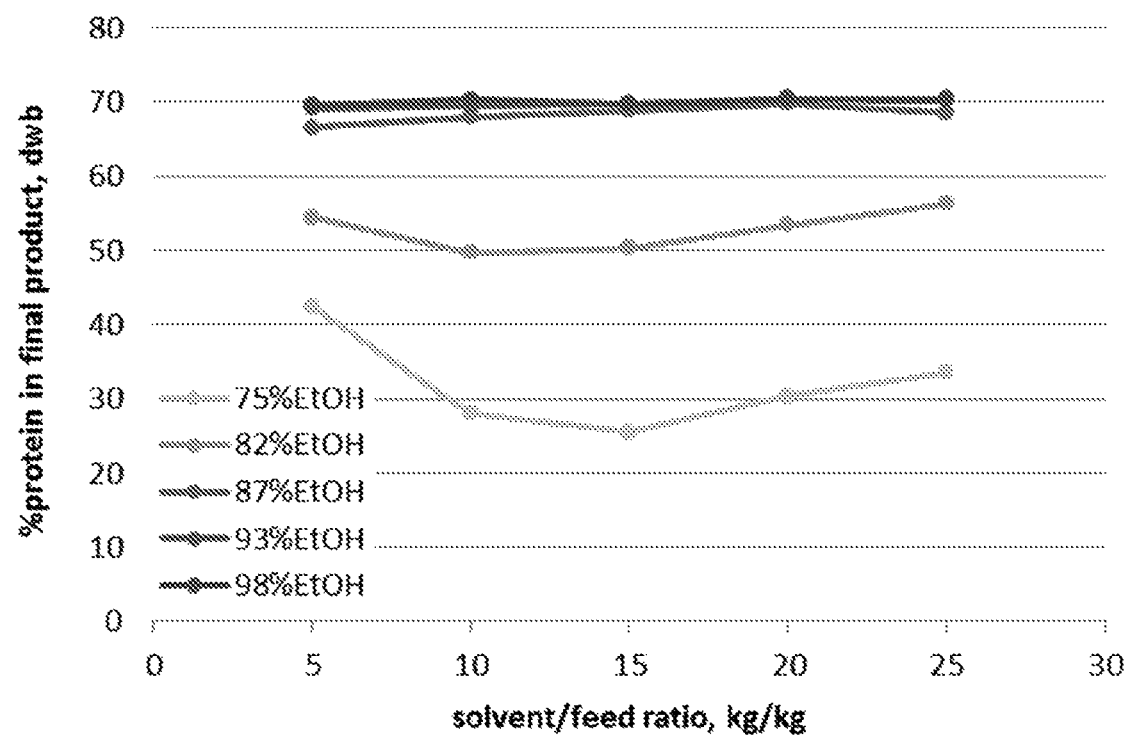
Figure 4A:
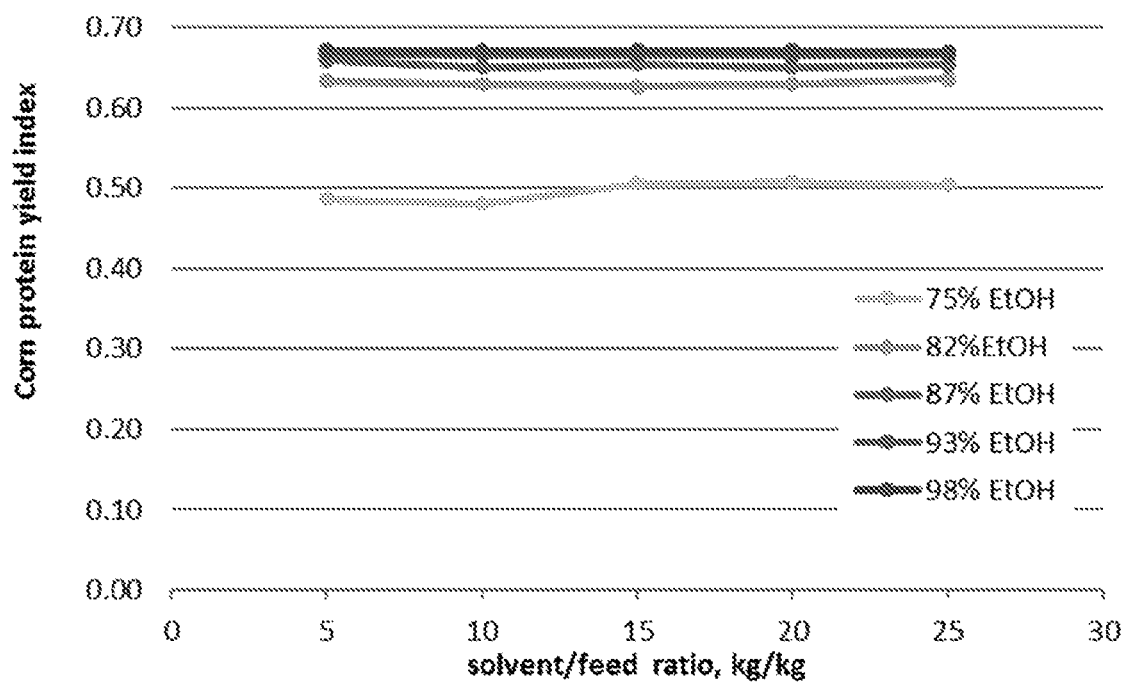
FIGS. 4A and 4B show ethanol concentration, solvent-feed ratio and temperature (25° C. left panel (4A); 42.5° C. right panel (4B)) during extraction impacts overall corn protein yield index.
Figure 4B:
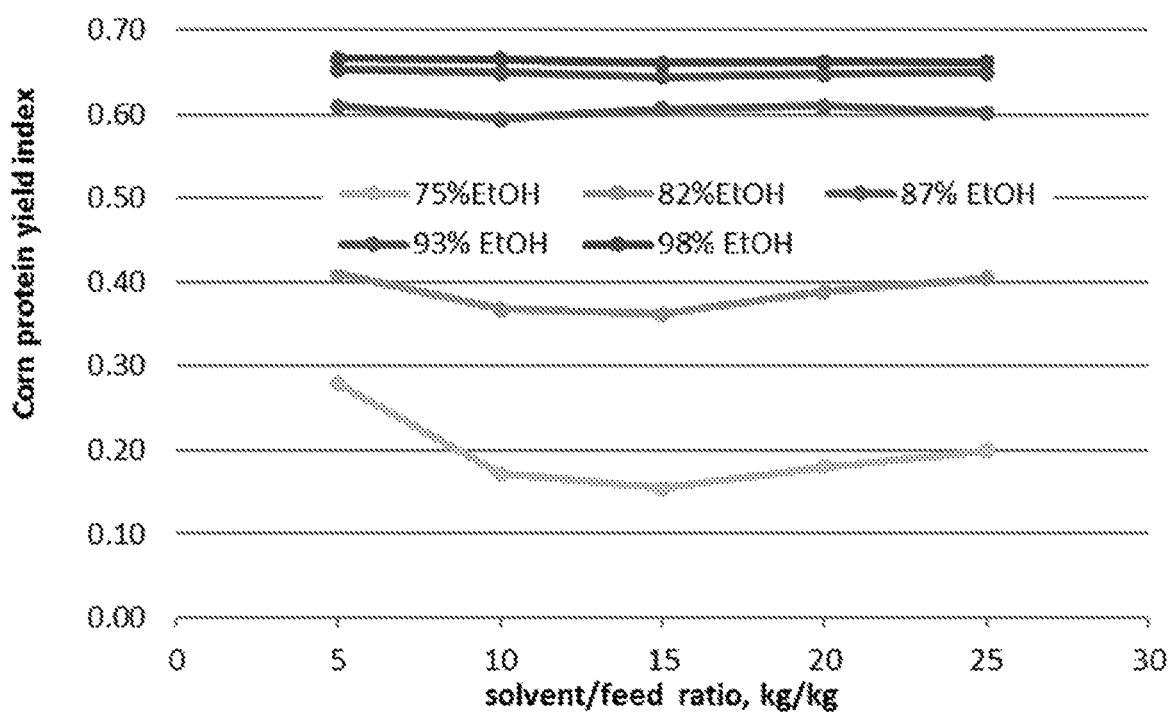
Figure 5:
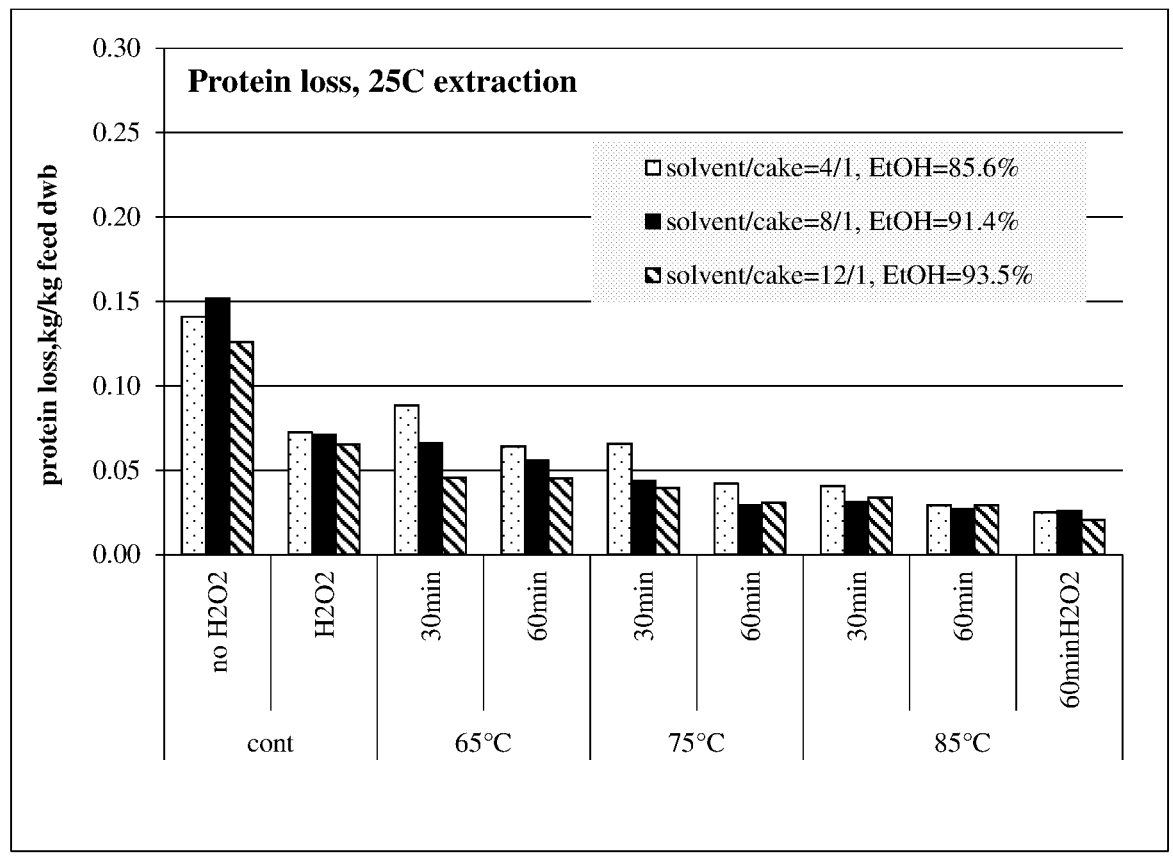
FIGS. 5-7 show holding the slurry at elevated temperatures or treating the slurry with H2O2 prior to extraction reduced protein loss. H2O2 treatment had an additional benefit of reducing protein loss particularly at higher extraction temperatures.
Figure 6:
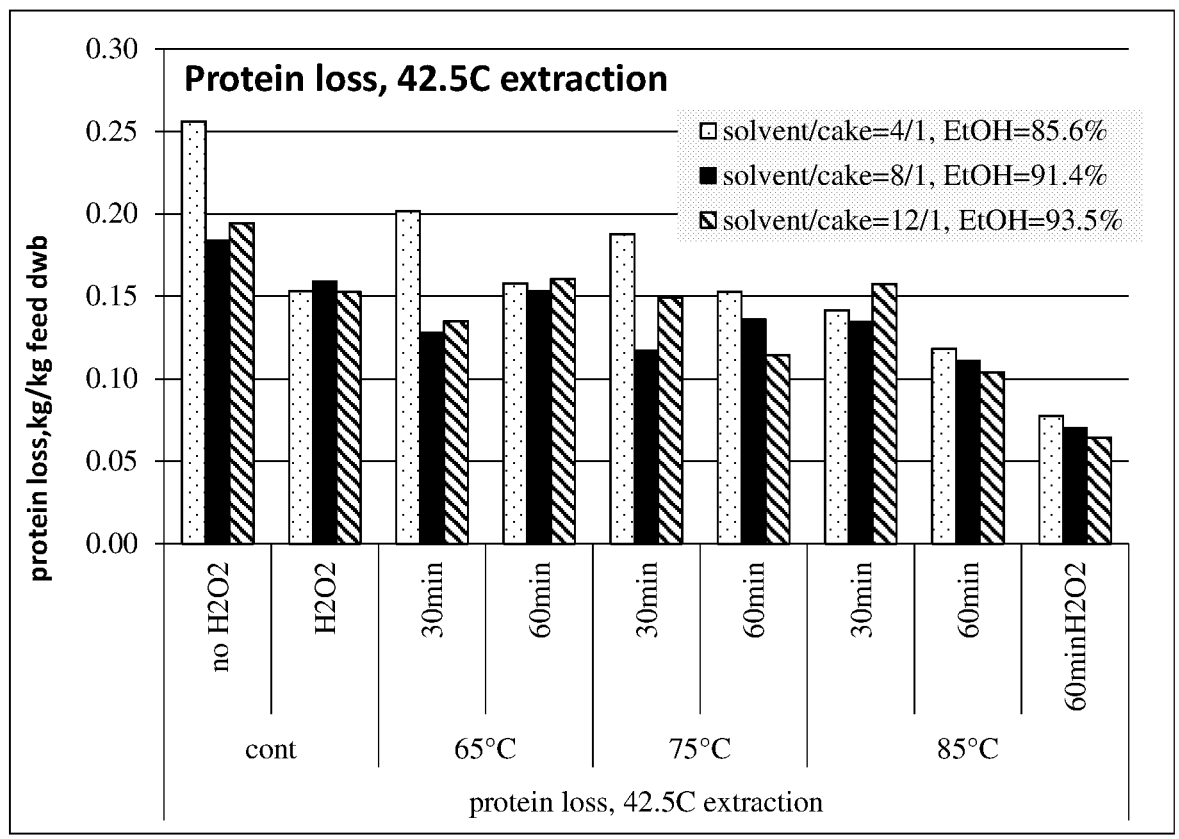
Figure 7:
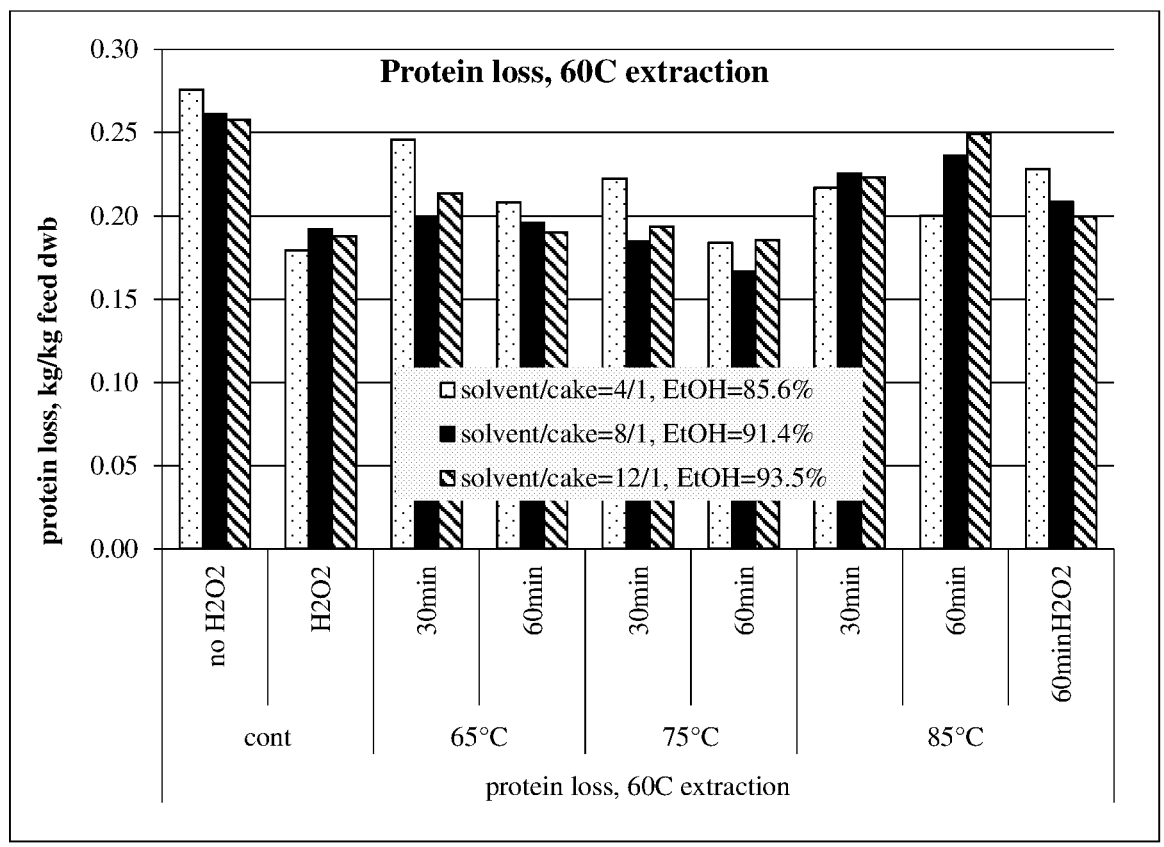
Figure 8:
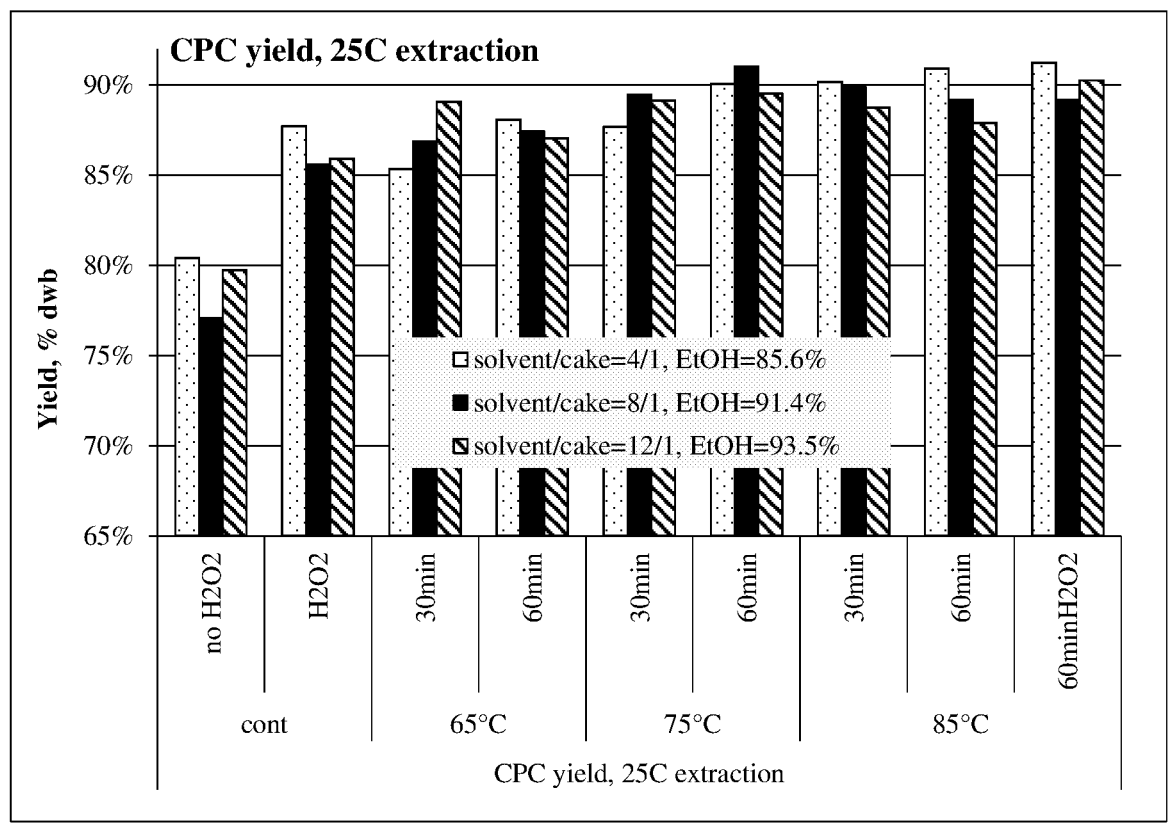
FIGS. 8-10 show the effects of holding the slurry at elevated temperatures or treating the slurry with H2O2 prior to extraction and the effects of ethanol concentration, solvent-feed ratio and temperature during extraction on the yield of the final corn protein concentrate product.
Figure 9:
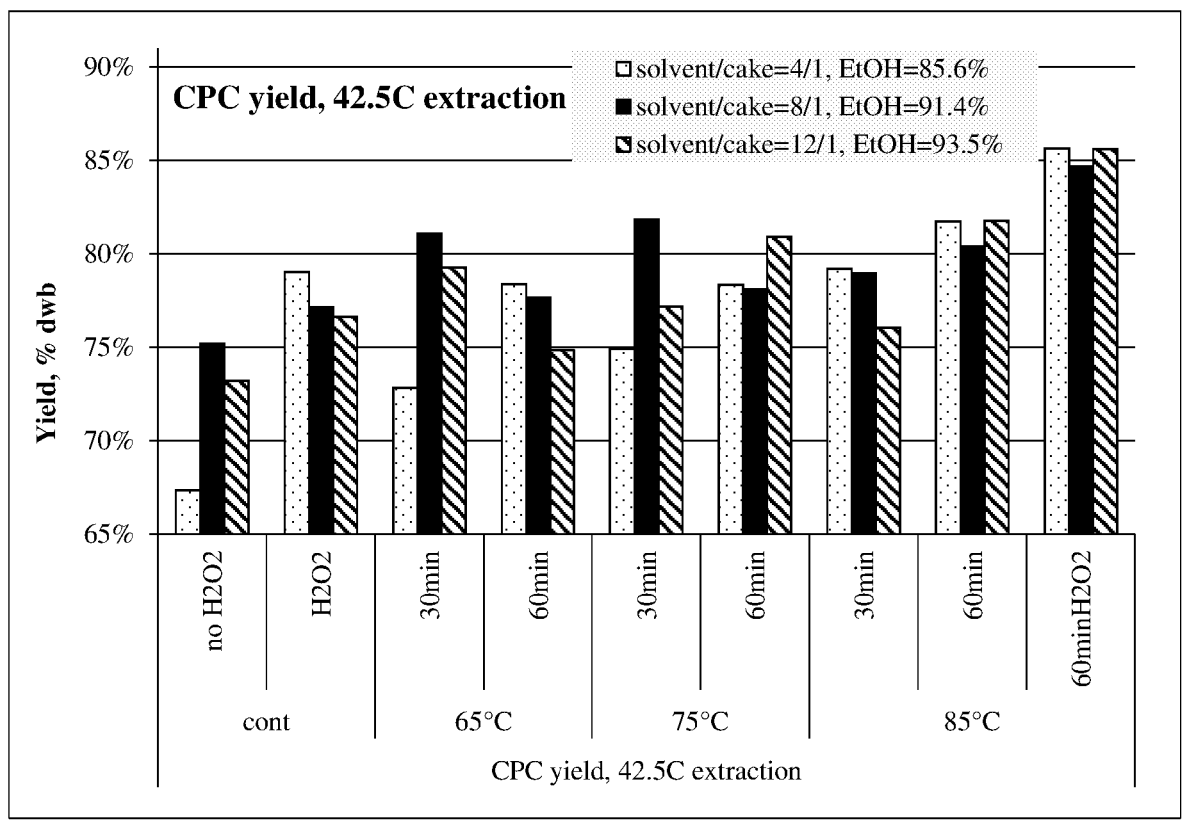
Figure 10:
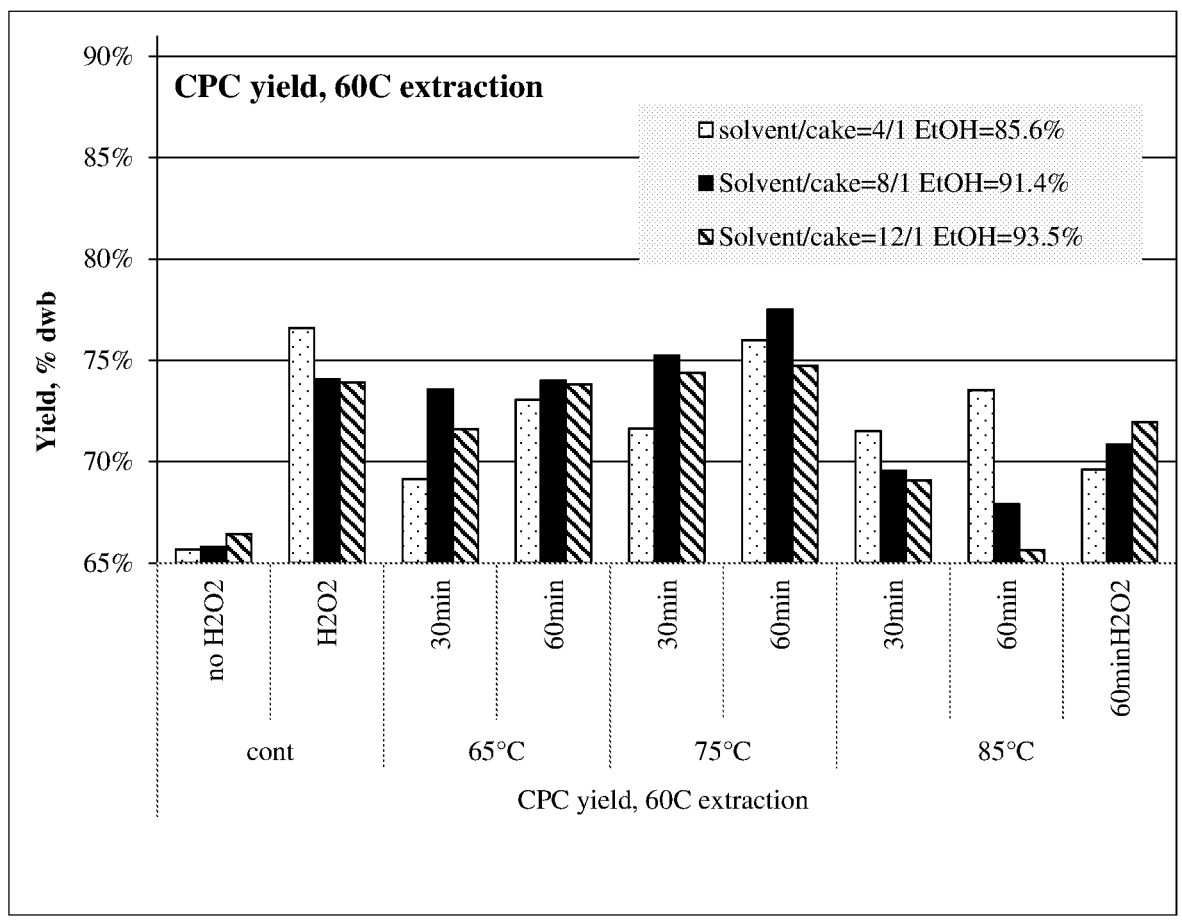
Figure 11:
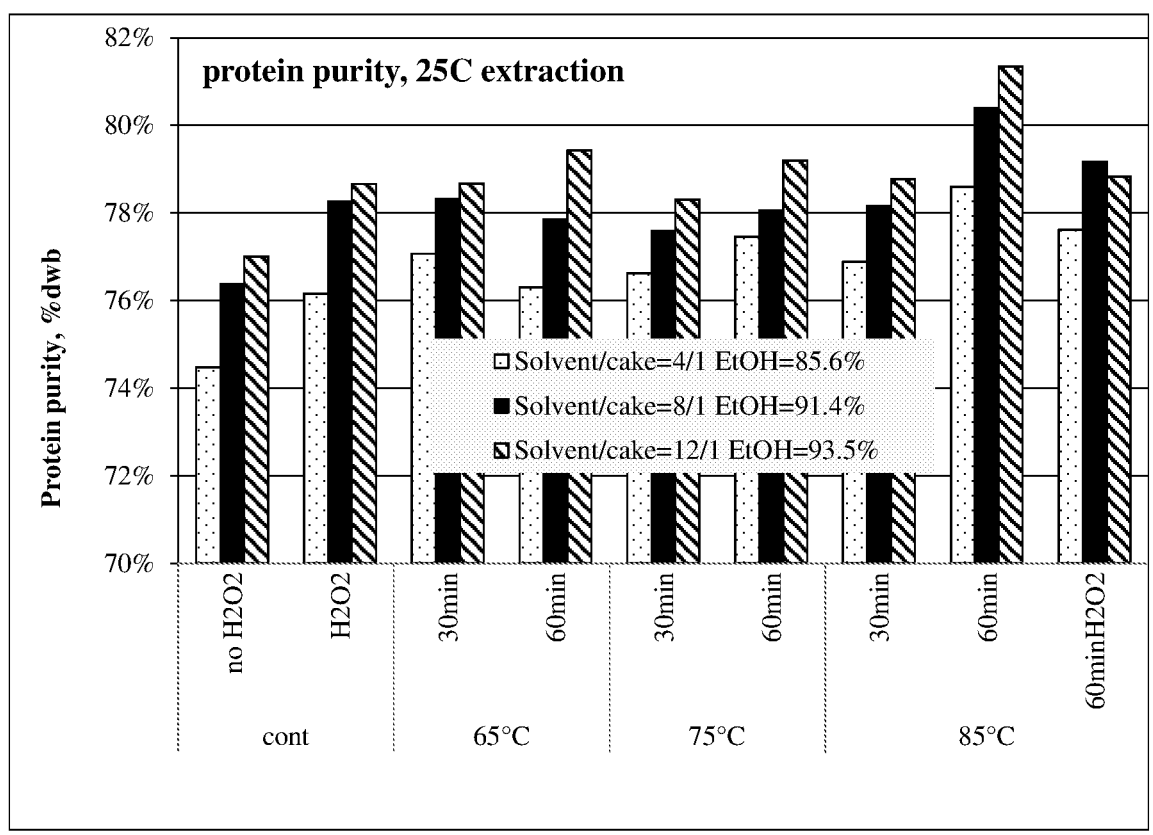
FIGS. 11-13 show the effects of holding the slurry at elevated temperatures or treating the slurry with H2O2 prior to extraction and the effects of ethanol concentration, solvent-feed ratio and temperature during extraction on protein concentration in the final corn protein concentrate product.
Figure 12:
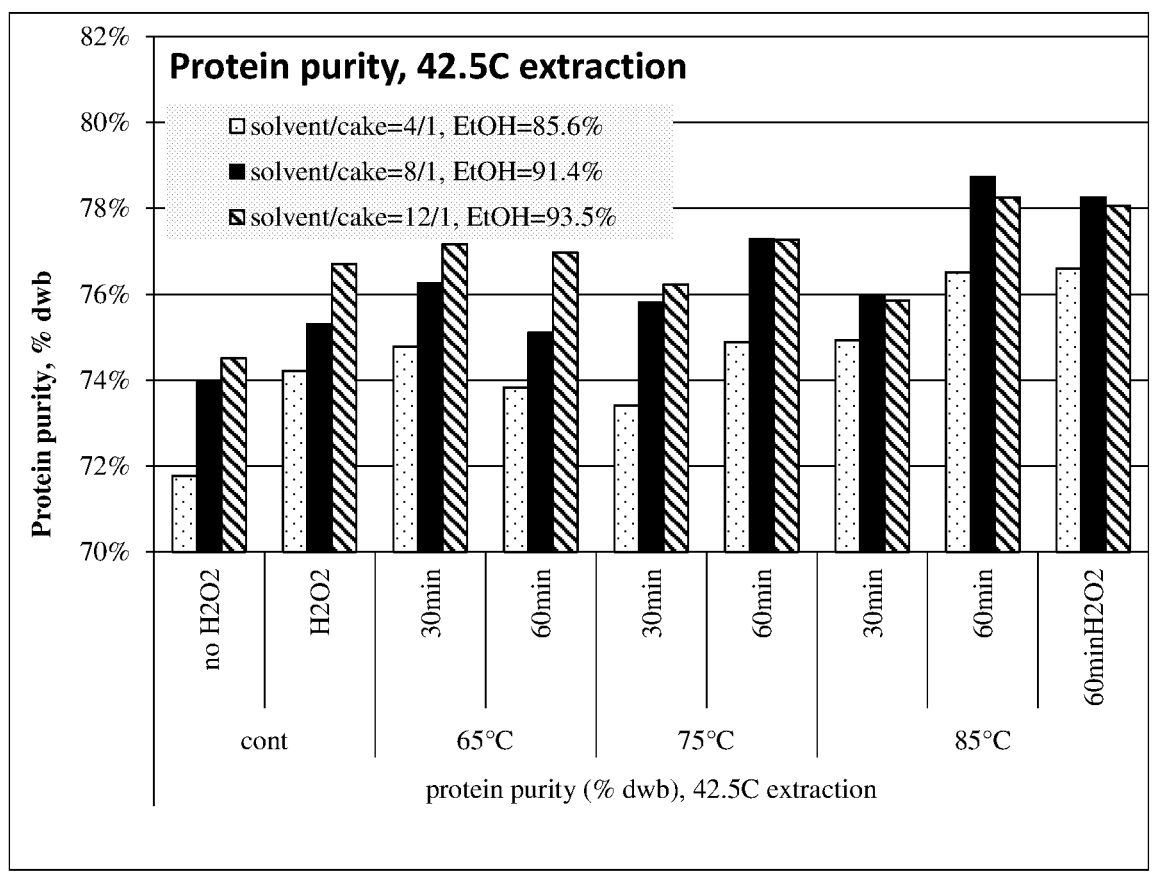
Figure 13:
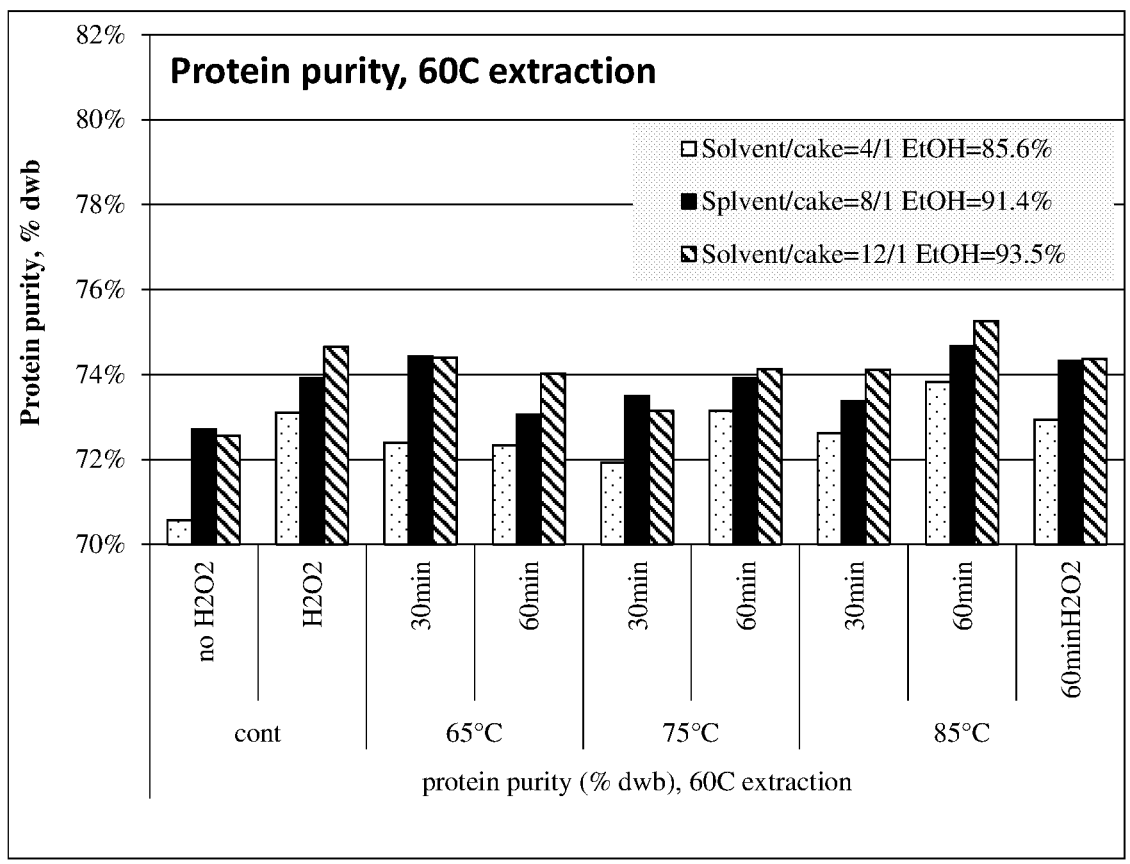
Figure 14:
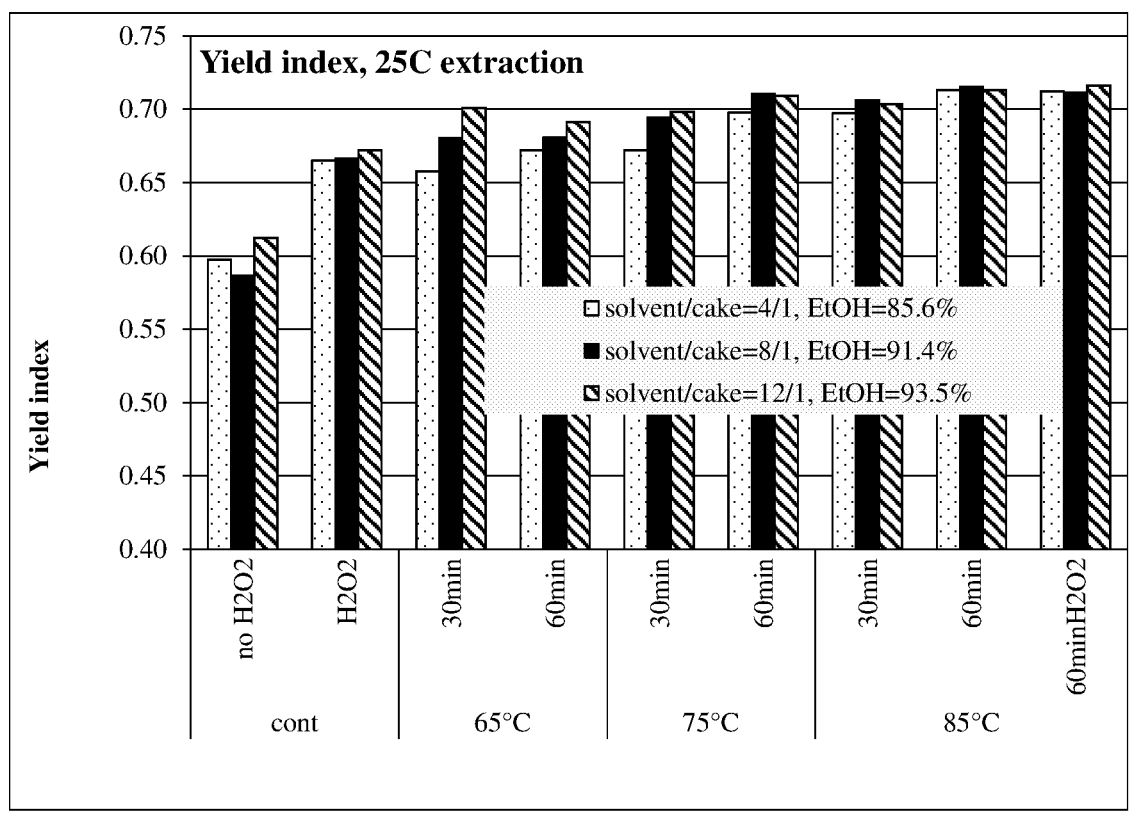
FIGS. 14-16 show the effects of holding the slurry at elevated temperatures or treating the slurry with H2O2 prior to extraction and the effects of ethanol concentration, solvent-feed ratio and temperature during extraction on corn protein yield index.
Figure 15:
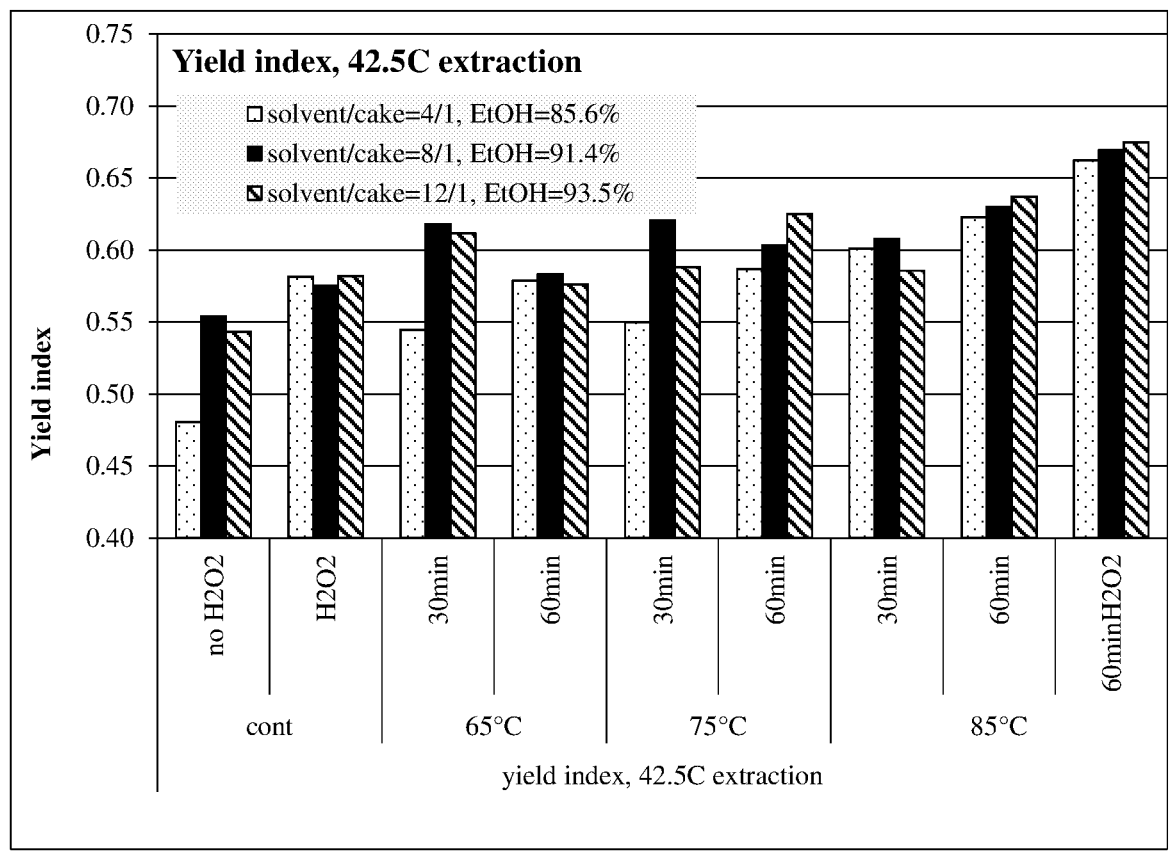
Figure 16:
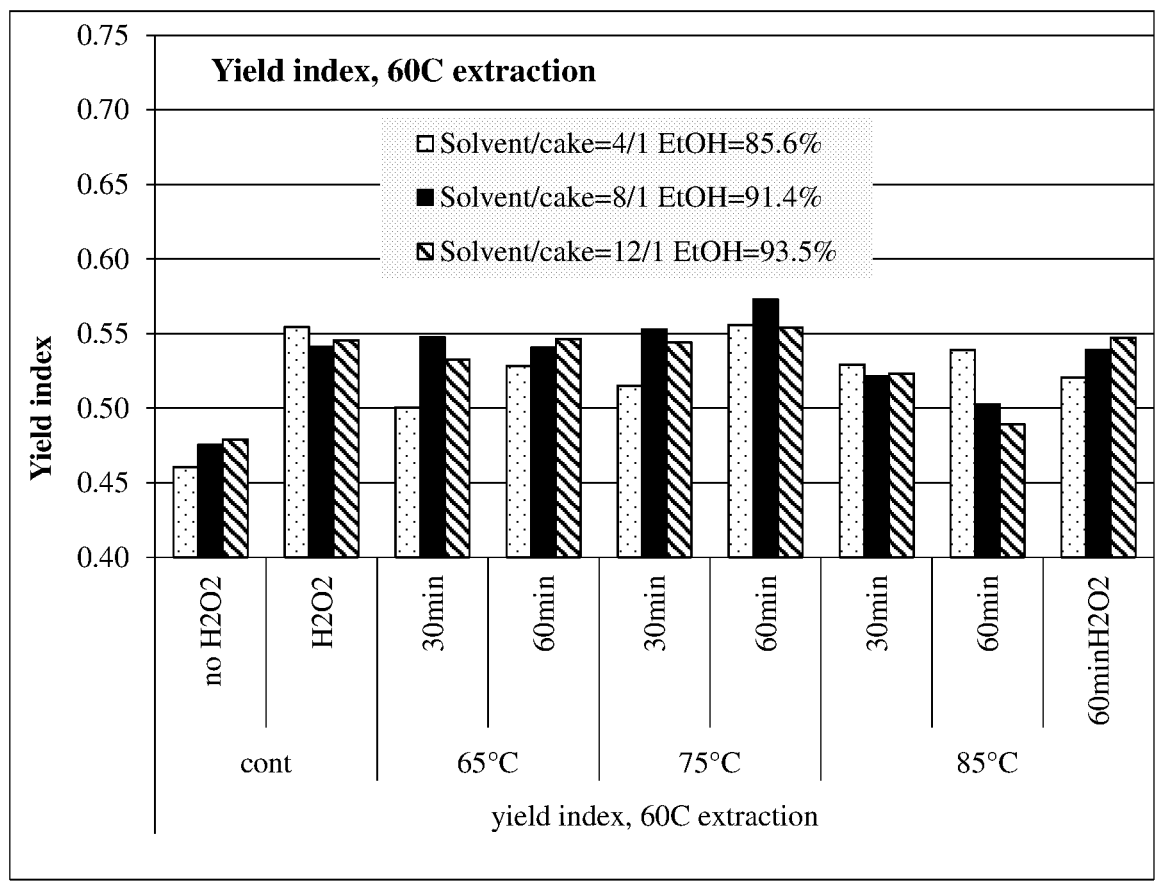

Results show extraction conditions, namely ethanol concentration, extraction temperature, and solvent-feed ratio all impact the yield and composition of final corn protein products with most significant effect found for temperature and ethanol concentration. Generally, higher ethanol (lower water), higher solvent-feed ratio and lower temperature resulted in higher yield and higher protein purity, leading to higher overall corn protein yield indices (FIGS. 2-4).

Example 2: Effect of Heat and H2O2 Treatment on Protein Solubilization by Ethanol Solvents at Different Temperatures Corn gluten slurry containing 800 ppm SO2 was obtained from the Cargill corn milling plant in Dayton, Ohio. The corn gluten slurry was either directly used (no heat treatment, control) or divided into 1-L polypropylene bottles. For control, 2 samples were prepared. The non-H2O2 control was obtained by immediate centrifugation. The H2O2-control sample was obtained by adding H2O2 solution (30% active H2O2, wt/wt) to the slurry (final active H2O2 was 600 ppm) followed by mixing at ambient temperature for 15 min then centrifugation. For heat treatments, the bottles contain the slurry with or without H2O2 addition (final active H2O2 was 600 ppm) were horizontally placed in a shaker set at 100 rpm and either 65° C. or 75° C. for 30 min or 1 hour. For 85° C. treatment, the bottles were placed in a water bath maintained at 85° C. with overhead mixing for 30 min or 1 hour. After treatment, the slurry was centrifuged at 4500 rpm for 5 min and liquid decanted. The wet cake was placed in a fume hood to further dry down to about 60% moisture levels measured by Mettler-Toledo moisture analyzer at 110° C. The wet caked was transferred to sealed plastic bags and stored in a refrigerator for subsequent solubility tests.

For solubility tests, 3 g, or 4.5 g or 8 g samples were weighted into 50-ml test tubes then 32 g or 36 g solvent of 98% (wt/wt) aqueous ethanol was added to the test tubes thus creating 3 solvent-cake ratios of 12 to 1, 8 to 1, and 4 to 1 with final solvent EtOH concentration in the system being 85.6-93.5% (wt/wt) respectively. Table 2 summarizes various aspects of the matrix compositions. The test tubes were tightly capped then horizontally placed in a shaker set at ambient temperature (~25° C.), or 42.5° C. or 60° C. and gently (60 rpm) shaken in orbital motion for 30 min followed by centrifugation at 4000 rpm for 5 min. The liquid was carefully collected and about 2 ml was analyzed for dry solid and protein.

TABLE 2

Solubility test matrix compositions.

| The solvent | | | Ratios (wt/wt) | | |
| --- | --- | --- | --- | --- | --- |
| g solvent/ g feed (58% DS) | % (wt/wt) EtOH in final solvent | EtOH/ water (wt/wt) | g solvent/ g DS | g EtOH/ g DS | g Water/g DS |
| 4 | 85.6 | 9.2 | 10.8 | 9.2 | 1.5 |
| 8 | 91.4 | 18.4 | 20.3 | 18.4 | 1.7 |
| 12 | 93.5 | 27.7 | 29.8 | 27.7 | 1.9 |

Again, protein loss due to solubilization was promoted by higher water concentration and higher extraction temperatures. Furthermore, data shows higher holding temperatures and longer holding time at a given temperature prior to de-watering results in lower protein loss when extraction was done at 25° C. A similar trend was found for 42.5° C. but to a lesser extent. When extraction was carried out at 60° C., holding at 85° C. had lower protein loss than the control but higher protein loss than those held at 65° C. or 75° C., and little difference was found between those holding at 65° C. and 75° C. Results also show that neutralization of SO2 by H2O2 treatment reduced protein loss across all three ethanol concentrations and extraction temperatures. Data also suggests holding the H2O2-treated slurry at elevated temperature for prolonged periods of time has additional benefits of reducing protein loss, increasing yield and protein purity in the final product, resulting in increased overall corn protein yield indices (FIGS. 5-16).

The invention claimed is:

1. A method of maintaining corn protein yield during extraction, comprising:
   obtaining a corn gluten material;
   heat treating the corn gluten material;
   treating the corn gluten material with hydrogen peroxide; and
   washing the corn gluten material to remove non-protein components with an ethanol-water solvent comprising at least 85 wt % ethanol to obtain a corn protein concentrate product;
   wherein the loss of corn protein content during extraction is less than 25% of total corn protein, and
   wherein the heat treating step is carried out before the washing step, the temperature of the heat treating step ranges from 55° C. to 85° C., the hydrogen peroxide treating step is carried out before the washing step, and the hydrogen peroxide is added to the corn gluten material at a molar ratio of 0.5-5.0.

2. The method of claim 1 wherein the ratio of solvent to corn gluten material ranges from 5:1 to 25:1.

3. The method of claim 1 wherein the heat treating step is applied after the hydrogen peroxide treating step.

4. The method of claim 1 wherein the ethanol-water solvent comprises at least 90 wt % ethanol.

5. The method of claim 1 wherein the ethanol-water solvent comprises at least 93 wt % ethanol.

6. The method of claim 1, wherein the ethanol-water solvent comprises at least 97 wt % ethanol.

7. The method of claim 1 where the corn protein yield index is from about 0.55-0.75.

8. The method of claim 1 wherein the corn gluten material comprises 50-70 wt % protein on a dry weight basis.

9. The method of claim 1 wherein the corn protein concentrate product comprises 55-85 wt % protein on a dry weight basis.

10. The method of claim 1 wherein the corn protein concentrate product is for human and animal consumption.

* * * * *